Figure 1:
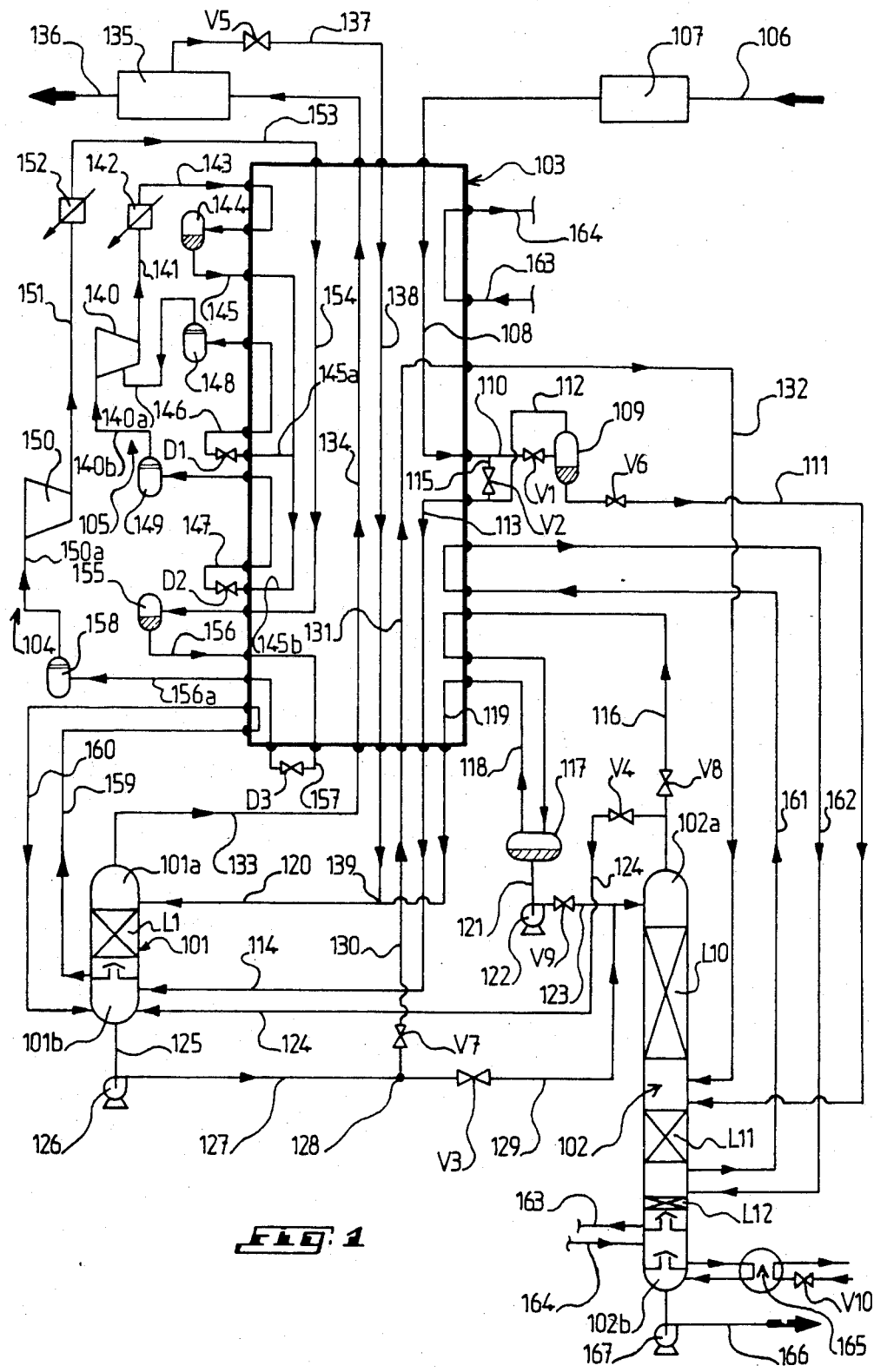

United States Patent [19]

Paradowski et al.

[11] Patent Number: 4,689,063
[45] Date of Patent: Aug. 25, 1987

[54] PROCESS OF FRACTIONATING GAS FEEDS AND APPARATUS FOR CARRYING OUT THE SAID PROCESS

[75] Inventors: Henri Paradowski, Cergy Pontoise; Hervé Parfait, Paris; Joëlle Castel, Port Marly; Alain Vasseur, Paris, all of France

[73] Assignee: Compagnie Francaise d'Etudes et de Construction "Technip", Paris, France

[21] Appl. No.: 836,140

[22] Filed: Mar. 4, 1986

[30] Foreign Application Priority Data

Mar. 5, 1985 [FR] France ............... 85 03222

[51] Int. Cl.$^4$ .................................................. F25J 3/02
[52] U.S. Cl. ........................................... 62/28; 62/32; 62/40; 62/42
[58] Field of Search ............... 62/23, 27, 28, 32, 40, 62/42

[56] References Cited

U.S. PATENT DOCUMENTS

| | | | |
|---|---|---|---|
| 3,542,673 | 11/1970 | Ringler | 62/23 |
| 3,656,312 | 4/1972 | Streich | 62/23 |
| 3,808,826 | 5/1974 | Harper et al. | 62/23 |
| 3,919,853 | 11/1975 | Rojey | 62/23 |
| 4,070,165 | 1/1978 | Colton | 62/23 |
| 4,203,742 | 5/1980 | Agnihorti | 62/23 |
| 4,251,249 | 2/1981 | Gulsby | 62/28 |
| 4,256,476 | 3/1981 | Van Buash | 62/23 |
| 4,285,708 | 8/1981 | Politte et al. | 62/23 |
| 4,322,225 | 3/1982 | Bellinger et al. | 55/27 |

Primary Examiner—Ronald C. Capossela
Attorney, Agent, or Firm—Kenyon & Kenyon

[57] ABSTRACT

The present invention relates to a process and an apparatus for cryogenic fractionation of gas feeds, the apparatus comprising essentially a contact purifying-refrigerating column associated with a fractionating column, an exchange system, a plurality of ducts with valves connecting the above three elements and two closed end independent refrigerating circuits integrated to the exchange system.

16 Claims, 2 Drawing Figures

PROCESS OF FRACTIONATING GAS FEEDS AND APPARATUS FOR CARRYING OUT THE SAID PROCESS

The present invention has essentially for its subject matter a process of cryogenic fractionation of any gas feeds such as for example natural gases, gases associated with hydrocarbon condensates, or gases resulting from the processing of petroluim fractions.

The invention is also directed to an apparatus for carrying out the said process.

Industrial apparatuses have already been proposed allowing the extraction either of ethane and compounds heavier than ethane, or of propane and compounds heavier than propane, as desired.

As a rule, in such known apparatuses, the gas feed is partially condensed throuh low-temperature cooling and then separated in a separating receiver. Thereafter, the liquid portion is processed in a conventional fractionating column and the desired heavy compound or compounds of the feed are recovered at the bottom of this column in liquid form. In some cases, a refrigerating cycle is provided to meet the need for cold in the apparatus.

However, apparatuses of such kind do not allow extracting more than 95% of the propane and more than 85% of the ethane contained in the feed, and are not, therefore, of excellent efficiency.

Furthermore, in French patent application No. 84.14996 filed on Sept. 28, 1984, in the name of the applicant, it was proposed to replace the separating receiver of the conventional apparatuses with a contact purifying-refrigerating column into which the partially condensed gas feed is introduced to be processed therein.

However, an apparatus with a purifying-refrigerating column as described in the aforesaid French patent application, only allows extracting a single cut, e.g. propane and compounds heavier than propane ($C_3+$ cut), which means that it does not allow extracting in the same unit either propane and compounds heavier than propane, or ethane and compounds heavier than ethane.

This is a shortcoming which the present invention is intended to remove by providing a process and an apparatus which offer great flexibility in use owing to the fact that they allow immediate switching from the extraction of the $C_3+$ cut to the extraction of the $C_2+$ cut, or vice versa, and that, moreover, efficiencies of 99% for the cut $C_3+$ and of 95% for the cut $C_2+$ can be reached easily.

To this end, the invention has for its subject matter a process of fractionating gas feeds, allowing the extraction of either compounds heavier than methane (cut $C_2+$) or of compounds heavier than ethane (cut $C_3+$), and wherein the said cut $C_3+$ is extracted by injecting the partially condensed gas feed into the bottom of a contact purifying-refrigerating column which produces at its top residual gas and at its bottom a liquid which is injected into a fractionating column to obtain at the bottom of this column a liquid containing the said $C_3+$ cut and at its top a gas distillate which is condensed and injected as supply into the top of the purifying-refrigerating column, the said process being characterized in that the extraction of the said cut $C_3+$ is selectively permutable with the extraction of the $C_2+$ cut which can be obtained:

by recirculating a portion of the compressed residual gas which is condensed in an exchange system and then injected into the top of the purifying-refrigerating column, by injecting the gas distillate issuing from the fractionating column directly into the bottom of the purifying-refrigerating column, and by injecting the liquid issuing from the bottom of the purifying-refrigerating column directly into the top of the fractionating column.

The process of the invention is also characterized in that, in case it is desired to extract the $C_2+$ cut, the gas feed, after at least partial condensation in the exchange system, is separated, on the one hand, into a liquid phase injected at the middle of the fractionating column and, on the other hand, into a gaseous phase which is at least partially condensed in the said exchange system, and thereafter injected into the purifying-refrigerating column, whereas, in case it is desired to extract the $C_3+$ cut, the said gas feed partially condensed in the refrigerating exchange system is injected directly and without separation into the purifying-refrigerating column.

A complementary amount of cold or negative calories is obtained in the exchange system owing to a refrigeration system which, for the extraction of the $C_3+$ cut, operates as a single refrigerating circuit with several pressure levels, and which, for the extraction of the $C_2+$ cut, operates as to distinct refrigerating circuits, namely, the said single refrigerating circuit and a second refrigerating circuit with a single pressure level.

It should be specified here that, in the single refrigerating circuit operating for the extraction of the $C_3+$ cut or for the extraction of the $C_2+$ cut, use is preferably made of a medium composed of a mixture of slight hydrocarbons such as ethane and propane, of a molecular weight ranging from 30 to 40, or of a pure substance of the propane type.

In the said second refrigerating circuit operating for the extraction of the $C_2+$ cut, use is preferably made of a medium composed of a mixture of slight hydrocarbons such as methane, ethylene, ethane or propane, of a molecular weight ranging from 26 to 36, or of a medium composed of a pure substance of the ethylene or ethane type.

According to a modified form of embodiment of the process, and in case it is desired to extract the $C_2+$ cut, a portion of the gas feed is derived to ensure the reboiling of the fractionating column, the derived gas feed is mixed with the remaining portion of the gas feed previously and partially condensed in the exchange system, the mixture obtained is separated into a liquid phase and a gaseous phase, and the liquid phase is sub-cooled in the exchange system, whereas the gaseous phase is expanded and then mixed with the said sub-cooled liquid phase to constitute a combined phase which is injected into the purifying-refrigerating column under the upper packing layer, whereas in case the cut to be extracted is $C_3+$, the gas feed is not derived but condensed directly and partially in the exchange system, whereafter it is subjected to the aforesaid separation to form a gaseous phase which, after the aforesaid expansion, is injected directly into the purifying-refrigerating column under the upper packing layer, and a liquid phase is injected directly into the said purifying-refrigerating column under the medium packing layer thereof.

According to another feature of the invention, in case additional cold is needed, a refrigeration by a refrigerating circuit with several pressure levels, for example, is performed jointly with the said expansion.

According to another feature of the process of the invention, irrespective of the cut ($C_3+$ or $C_2+$) which it is desired to extract, the said fractionating column operates at a higher pressure than that of the purifying-refrigerating column to ensure the injection of the distillate issued from the fractionating column, either condensed or not, into the purifying-refrigerating column.

The invention is also directed to an apparatus for carrying out the above process, of the type including: a contact purifying-refrigerating column associated with a fractionating column; a duct for the supply of the liquid located at the bottom of the purifying-refrigerating column, the said duct connecting the latter column to the fractionating column through an exchange system; and a fractionating column distillate reflux duct connecting this column to the purifying-refrigerating column through the said exchange system, the said apparatus being essentially characterized in that it also includes:

at least one duct for recirculating a portion of the compressed residual gas, which duct passes through the exchange system and is connected to the top of the purifying-refrigerating column, at least one conduit for the injection of the distillate from the fractionating column directly and without passing through the exchange system, into the bottom of the purifying-refrigerating column, and at least one duct for the injection of the liquid from the purifying-refrigerating column, the said duct connecting, directly and without passing through the exchange system, the bottom of this column to the top of the fractionating column.

According to one form of embodiment, the gas feed condensed at least partially in the exchange system is supplied to a separator provided at its bottom with a duct connected directly and preferably to the middle of the fractionating column to inject therein the separated liquid phase, and at its top with a duct for the separated gaseous phase which passes through the exchange system and is followed by a duct connected to the purifying-refrigerating column to inject therein the said at least partially condensed gaseous phase, whereas means, such as for example valves, are provided to by-pass the said separator.

According to another feature of the apparatus of the invention, there are integrated to the said exchange system two closed and independent refrigerating circuits operating at a single pressure level and at one or several pressure levels, respectively.

According to another form of embodiment, the apparatus is characterized by a gas feed deriving duct connected to a reboiling system associated with the fractionating column and joining a duct through which the remaining portion of the gas feed passes, the junction of the said ducts communicating with a separator provided in its bottom portion with a liquid fraction flow path divided into two paths, one of which is connected to the said exchange system and the other is directly connected to the purifying-refrigerating column, whereas the top of the separator is connected through a duct to the inlet of a turbine expander whose outlet is connected to one of the said flow paths to thus constitute a mixture injected through a duct into the purifying-refrigerating column to which the said duct is connected.

It will be pointed out here that the refrigerating circuit, e.g. of the type with several pressure levels, is associated with the apparatus.

According to still another feature, the exchange system is constituted by at least one plate exchanger in which the temperature of the descending fluids diminishes and that of the rising fluids increases.

With the purifying-refrigerating column is advantageously associated a reboiler which forms part of the exchange system.

According to still another feature of the apparatus, the switching from the extraction of the $C_3+$ cut to the extraction of the $C_2+$ cut is merely effected by means of manual or powered control valves interposed on the aforesaid ducts.

Figure 2:
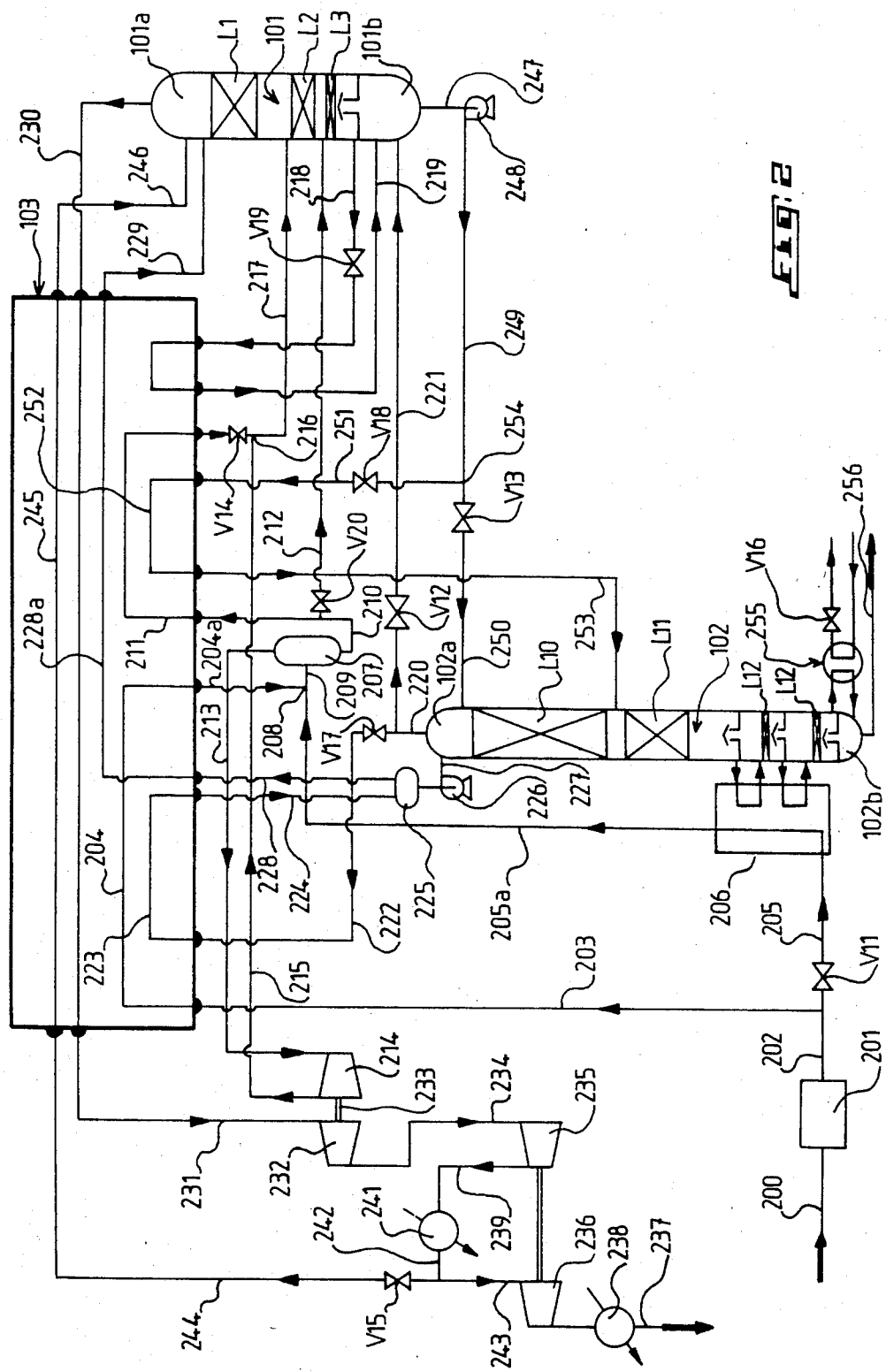

Other features and advantages of the invention will appear more clearly as the following detailed description proceeds with reference to the appended drawings given solely by way of example and wherein:

FIG. 1 is a diagrammatic view of one example of embodiment of an apparatus complying with the principles of the invention and using a refrigerating system with two refrigerating cycles, and FIG. 2 is a diagrammatic view of another example of embodiment of an apparatus according to the invention using a turbine expander.

Reference is first made to FIG. 1 which illustrates the principle of a unit for extracting ethane and compounds heavier than ethane ($C_2+$ cut) and of propane and compounds heavier than propane ($C_3+$ cut), with external refrigeration.

The apparatus includes essentially a contact purifying-refrigerating column 101 of the type described in the aforementioned French patent application, a fractionating column 102 and an exchange system 103 with which are associated two closed and independent refrigerating circuits designated generally by the reference numerals 104 and 105.

It will be noted that the column 101 is provided with an upper packing layer $L_1$, whereas the fractionating column 102 is provided with at least one upper packing layer $L_{10}$, one medium layer $L_{11}$ and one lower layer $L_{12}$.

The gas feed to be processed enters the apparatus through a duct 106 connected to a drying unit 107 which is followed by a passage path 108 passing through the exchange system 103 and leading to a separator 109 through a duct portion 110. The bottom of the separator 109 is connected through a duct 111 directly and preferably to the middle of the fractionating column 102. The top of the separator is provided with a duct 112 a portion 113 of which passes through the exchange system 103 and is extended by the duct portion 114, thus allowing the injection of the partially condensed gaseous phase into the bottom of the purifying-refrigerating column. A valve V1 is provided on the duct portion 110 and, as will be seen later, the separator 109 may be bypassed by a duct 115 connecting the duct portion 110 to the duct 113 and equipped with a valve V2.

The gaseous distillate from the top 102a of the fractionating column 102 is conveyed through a duct 116 passing through the exchange system 103 to a reflux receiver 117. This reflux receiver is provided at its top with a duct 118 for the supply of gaseous distillate which is cooled in the exchange system 103 by passing through the duct portion 119 to be condensed at least partially and thus injected through the duct portion 120 into the top 101a of the purifying-refrigerating column 101. The reflux receiver 117 is provided at its bottom with a second duct 121 equipped with a pump 122 and ensuring through the flow path 123 the reflux into the top 102a of the column 102.

A duct 124 deriving from the duct 116 allows the injection of the distillate from the fractionating column 102, directly and without passing through the exchange system 103, into the bottom 101b of the purifying-refrigerating column 101.

The liquid at the bottom of this column is recovered in a duct 125 and supplied by a pump 126 to the fractionating column 102 through 123.

More precisely, and as clearly seen in FIG. 1, the liquid leaving the pump 126 is conveyed to the column 102 through a duct 127 which, at 128, divides into two ducts, i.e., a duct 129 connected, directly and without passing through the exchange system 103, to the top 102a of the fractionating column 102 through 123, and a duct 130 including a conduit portion 131 passing through the exchange system 103 and which is followed by another duct portion 132 connected substantially to the middle of the fractionating column 102.

The residual gas leaving the top 101a of the column 101 flows through a duct 133 a portion 134 of which passes through the exchange system 103 to thereafter connect with a compression unit 135, whereafter the residual gas is discharged through a duct 136. A duct 137 connected to the compression unit 135 allows the recirculation of the compressed residual gas, a portion 138 of this duct extending through the exchange system 103 and being connected at 139 to the duct 120 for the supply of reflux distillate from the fractionating column 102 to the top of the purifying-refrigerating column 101.

The closed regrigerating circuit 105 includes a compressor 140, the discharge side of which is connected through a duct 141 to a condenser with refrigerant of external origin. This condenser 142 is connected by a duct 143 passing through the exchanger 103 to a receiver 144, the bottom of which is provided with a duct 145 which passes through the exchanger 103 to subcool the separated liquid phase. The duct 145 divides into two paths 145a, 145b, each equipped with an expansion valve $D_1$, $D_2$. The liquid phase is thus vaporized at two pressure levels before reaching, through the ducts 146, 147 passing through the exchanger 103, respectively, receivers 148, 149, which, in their turn, are connected through ducts 140a and 140b, respectively, to the intermediate stage and to the low-pressure stage of the compressor 140.

The other closed refrigerating circuit 104 associated with the exchanger 103 includes essentially a compressor 150, the discharge side of which is connected through a duct 151 to a condenser 152 with refrigerant of external origin. The outlet of the condenser 152 is provided with a duct 153 which passes by its portion 154 through the exchanger 103 and leads to a receiver 155. The bottom of this receiver is provided with a duct 156 passing through the exchanger 103 and then leaving the latter through a duct portion seen at 157 and provided with an expansion valve $D_3$. Thus, the subcooled liquid phase leaving the receiver 155 is expanded and vaporized in the duct portion 156a to thereafter reach a receiver 158 connected through the duct 150a to the suction side of the compressor 150.

A reboiler 159, 160 is associated with the bottom of the purifying-refrigerating column 101, the said reboiler forming part of the exchange system 103, according to the example illustrated in FIG. 1.

At 161 and 162 are shown ducts forming a loop connected to the fractionating column 102 and passing through the exchange system 103 to thus provide an intermediate reboiler capable of recovering additional cold or negative calories. With the bottom 102b of the fractionating column is associated, on the one hand, a reboiler constituted by ducts 163 and 164 passing through the hot section of the exchange system 103, and on the other hand, another reboiler with an external heating medium, generally designated at 165.

The liquid product collected at the bottom 102b of the fractionating column 102 is discharged through a duct 166 via a pump 167.

The apparatus just described also includes, in addition to the abovementioned valves V1 and V2, other valves the actuation of which will cause the apparatus to operate either in propane extraction mode ($C_3+$ cut) or in ethane extraction mode ($C_2+$ cut). Seen in FIG. 1 are a valve V3 on the duct 129, a valve V4 on the duct 124, a valve V5 on the duct 137, a valve V6 on the duct 111, a valve V7 on the duct 130, a valve V8 on the duct 116, a valve V9 on the duct 123, and a valve V10 on the external medium supply to the reboiler 165.

In the following is described the operation of the apparatus of FIG. 1 in the case of propane extraction and then in the case of ethane extraction, it being understood that the function and particular operation of the purifying-refrigerating column will not be examined at length here, since they have been described in the aforesaid French patent application in the name of the applicant.

The operation of the unit will be described with reference to a calculated example using natural gas of the following composition:
nitrogen: 2.3% mol
carbon dioxide: 0.3% mol
methane: 87.4% mol
ethane: 7.0% mol
propane: 2.1% mol
butane: 0.9% mol .

This gas is initially at a pressure of 30 bar and has a temperature of 15° C.

There will first be described the operation of the apparatus for extracting propane and compounds heavier than propane ($C_3+$).

In this mode of operation, the valves V1, V3, V4, V5 and V6 are closed and all the other valves are open.

The dried gas feed is refrigerated at high pressure in the exchange system 103 which is constituted by a plate exchanger in which the temperature of the descending fluids decreases and the temperature of the rising fluids increases. More precisely, the dried gas passes through the ducts 108 and 113 (valve V1 closed, valve V2 open), where it is cooled down to −68° C. Thereafter, the gas feed is introduced through the conduit 114 into the bottom 101b of the purifying-refrigerating column where it contacts the reflux 120 constituted by the gaseous distillate 118 partially condensed at 119 at −70° C.

The condensates collected at 125 at the bottom of the purifying column 101 are pumped at 126 and then warmed up through the pipe 131 to 10° C. under 30.3 bars before being fed to the fractionating column 102 through the duct 132.

The top 102a of the fractionating column 102 is provided with a condensation system integrated to the exchange system 103 or located inside the said column, so that the distillates leaving it through the conduit 116 are condensed at −31° C. before being introduced into the receiver 117 to produce the gas reflux flowing through the duct 118 and the liquid reflux flowing through the duct 121, the pump 122 and the duct 123 to thus return to the top 102a of the column 102.

The residual gas leaving the purifying-refrigerating column 101 through the duct 133 recovers negative calories passing through the duct 134 extending through the exchanger 103, and is supplied at 45° C. to the compression section 135, 136, where it is brought to a pressure of 65 bars.

The reboiling of the fractionating column 102 is ensured by the external fluid passing through the reboiler 165, and the $C_3+$ cut obtained at the bottom 102b of the column 102 is available at a pressure of 30.5 bars and a temperature of 60° C. It will be noted here that, in the propane extraction case described here, the reboilers 161, 162, on the one hand, and 163, 164, on the other hand, are not used. The same applies to the separator 109, as explained earlier. As for the refrigeration necessary for the operation of the apparatus, it is only ensured by the refrigerating cycle 105 using preferably a refrigerating mixture of ethane (47% mol) and propane (53% mol).

This mixture, on leaving the compressor 140, is at a pressure of 30 bars and is partially condensed in the air refrigerating means 142 at 49° C., and is thereafter entirely condensed in the upper hot portion of the exchanger 103 before being introduced into the receiver 144. The liquid leaving this receiver is subcooled in the exchanger 103 and then expanded and cooled at two different pressure levels (streams 146 and 147) so as to ensure the necessary refrigeration.

There will now be described the mode of operation of the apparatus for extracting ethane and compounds heavier than ethane ($C_2+$ cut).

In this specific case, it is merely necessary to close the valves V2, V7, V8, V9 and V10, whereas all the other valves V1, V3, V4, V5 and V6 are opened.

The gas feed dried at 107 is cooled down to −60° C. at a high pressure in passing through the duct 108 in the plate exchanger 103, whereafter the said feed is introduced into the separating receiver 109 (valve V1 open, valve V2 closed). The liquid phase 111 is directly injected into the column 102. As for the vapor phase 112 passing through the duct 113 is cooled down to 91.7° C. and introduced through the duct 114 into the bottom of the purifying-refrigerating column 101 where it contacts the at least partially condensed refrigerating fluid 120 which, as mentioned earlier, is produced by the recirculation at high pressure (43.7 bars) of a fraction 137 of the residual gas withdrawn from the intermediate stage of the compression section 135, 136, which fraction is entirely condensed at 138 in the exchanger 103 before entering the column 101 through the conduit 120.

Here the stream at the bottom of the column 101 is heated and partially vaporized in the exchange system 103 (ducts 159, 160), to ensure the reboiling of the said column 101.

From the bottom of this column, the liquid is supplied by the pump 126 directly to the top 120a of the fractionating column 102 through the ducts 127 and 129 (valve V3 open, valve V7 closed).

The intermediate reboiler 161, 162 allows recovering additional negative calories, whereas the reboiling 163, 164 of the column 102 takes place in the hot upper portion of the exchanger 103, up to 20° C.

The $C_2+$ cut is collected at 166 at a temperature of 20° C. and a pressure of 30 bars, and the top 102a of the column 102 directly feeds the bottom of the purifying-refrigerating column 101 through the duct 124 (valve V4 open, valve V8 closed).

The residual gas leaving the column 101 through the duct 133 recovers negative calories in the exchanger 103 by passing through the duct 134 and is supplied at 40° C. to the compression section 135, 136 to be brought to a pressure of 65 bars.

The refrigeration necessary for the operation of the unit in $C_2+$ cut extraction mode is ensured by the refrigerating cycle 105, as also by the refrigerating cycle 104.

The refrigerating cycle 104 preferably uses a refrigerating mixture of ethylene (99% mol) and propane (1% mol).

At the discharge of the compressor 150, this refrigerating mixture is at a pressure of 30 bars and is cooled to 49° C. in the air refrigerating means 152. Thereafter, owing to the refrigerating cycle 105, the aforesaid refrigerating mixture is entirely condensed when it reaches the receiver 155. The liquid 156 leaving this receiver is thereafter subcooled to −94° C. by passing through the exchanger 103 and is thereafter expanded to 1.6 bar (D3) and vaporized up to −65° C. to ensure the necessary refrigeration of the lower and cold portion of the exchanger 103.

As for the refrigerating cycle 105, it operates exactly as described previously in connection with the operation of the apparatus in the $C_3+$ cut extraction mode; however, in case of operation of the apparatus in the $C_2+$ cut extraction mode, the refrigerating mixture flowing through the circuit 105 is preferably constituted by a mixture of ethane (50% mol) and propane (50% mol).

Reference is now made to FIG. 2 to describe the structure and operation of a second form of embodiment of the apparatus complying with the principles of the invention and using at least one turbine expander.

As in the above-described form of embodiment, this apparatus includes essentially a contact purifying-refrigerating column 101, a fractionating column 102 and an exchange system 103. It will be noted that the column 101 is provided with an upper packing layer $L_1$ and at least one medium and one lower packing layer $L_2$ and $L_3$, respectively, whereas the fractionating column 102 is provided with at least one upper, one medium and one lower packing layer $L_{10}$, $L_{11}$ and $L_{12}$, respectively. This apparatus, as the one illustrated in FIG. 1, allows by itself, by means of simple adjustments, switching from one extraction mode to another, i.e., from the extraction of a $C_3+$ cut to the extraction of a $C_2+$ cut.

The gas feed reaches the apparatus through a duct 200 connected to a drying unit 201 provided with a dried-gas outlet path 202, which path divides into two ducts, namely a column 203 which is followed by a portion 204 of the exchange system 103, itself followed by a duct portion 204a; and a deriving or branch duct 205 passing through a reboiling system 206 associated with the fractionating column 102, the said duct 205 being extended by a portion 205a which leads to a phase separator 207. The conduit portion 204a is connected at 208 to the duct portion 205a upstream of the separator 207 to form a single duct 209 communicating with the said separator.

The bottom of the said separator 207 is provided with an outflow path 210 which divides into two paths, namely, a path 211 passing through the exchange system 103 and a path 212 directly connected to the purifying-refrigerating column 101.

The top of the separator 207 is connected through a duct 213 to the inlet of a turbine expander 214 whose outlet is connected through a duct 215 to the aforesaid outflow path 211. More precisely, the path 211 extending from the exchange system 103 is connected to the duct 215 at 216 to thus provide a mixture which is injected by a single duct 217 into the contact purifying-refrigerating column 101. This column is fitted with a reboiling system constituted by the ducts 218, 219 which form a loop passing through the exchange system 103.

The top 102a of the fractionating column 102 is provided with a distillate outflow path 220 which divides into two ducts, namely, a duct 221 which does not pass through the exchange system 103 and which allows injecting the distillate directly into the bottom 101b of the purifying-refrigerating column 101, and a duct 222 connected to the portion 223 of the exchange system 103.

The portion 223 of the said exchange system is connected through a duct 224 to a reflux receiver 225, the bottom of which is connected through a duct 227, via a pump 226, to the top 102a of the column 102 into which is thus injected the liquid phase from the receiver 225.

The gaseous phase from the receiver 225 is conveyed through a conduit 228 to a portion 228a of the exchange system 103, and is thereafter injected through a conduit 229 into the top 101a of the purifying-refrigerating column 101.

The top 101a of this column is connected to a duct 230 for the passage of the residual gas through the exchanger 103, whereafter the duct 231 at the outlet of the exchanger 103 is connected to the suction side of a compressor 232 coupled with the turbine expander 214, as shown diagrammatically at 233.

The discharge side of the compressor 232 is connected through a duct 234 to the suction side of the first stage 235 of the compression section and thereafter to the second stage 236 of the compression section through a duct 239 via an exchanger 241, the residual gas being discharged through a conduit 237 provided with a final exchanger, refrigerating system 238. The outlet duct 242 of the exchanger 241 divides into two branches, namely, a duct 243 connected to the suction side of the second compression stage 236 and a residual gas recirculating duct 244 which is followed by a portion 245 of the exchange system 103, itself followed by a duct 246 connected to the top 101a of the purifying-refrigerating column 101.

The liquid at the bottom 101b of this column is collected in a duct 247 provided with a pump 248 whose outlet is provided with a duct 249 which divides into two flow paths, namely, a duct 250 directly connected to the top of the fractionating column 102 and a duct 251 followed by a portion 252 of the exchange system 103, itself followed by a duct 253 connected substantially to the middle of the said column 102. At 254 is shown the point of junction of the duct 250, on the one hand, and the ducts 251, 252, 253, on the other hand.

A reboiler 255 is associated with the bottom 102b of the column 102, and the heavy compounds collected from the bottom of this column are discharged through a duct 256.

The apparatus just described includes a plurality of manual or powered control valves which allow operating the apparatus in such a manner as to extract either the $C_3+$ cut or the $C_2+$ cut, as appears from FIG. 2 showing a valve V11 on the branch duct 205, a valve V12 on the duct 221, a valve V13 on the duct 250, a valve V14 on the duct 211, a valve V15 on the duct 244, a valve V16 on the passage path of the external fluid in the reboiler 255, a valve V17 on the duct 222, a valve V18 on the duct 251, a valve V19 on the reboiler 218–219, and a valve V20 on the duct 212.

In the following, the operation of the apparatus just described in propane extracting mode and in ethane extracting mode is explained with reference to a calculated example using natural gas of the following composition:

nitrogen: 2.3% mol
carbon dioxide: 0.3% mol
methane: 87.4% mol
ethane: 7.0 mol
propane: 2.1% mol
butane: 0.9% mol The natural gas is introduced into the apparatus through the duct 200 at a temperature of 15° C. under a pressure of 50 bars.

For the extraction of propane and of compounds heavier than propane ($C_3+$ cut), the valves V11, V12, V13, V14 and V15 are closed, whereas the valves V16, V17, V18, V19 and V20 are opened.

The gas feed dried at 15° C. and at high pressure at 201 flows through the ducts 202 and 203 and is then partially condensed at 204 in the plate exchanger 103 down to a temperature of −40° C., whereafter it is introduced into the separating receiver 207. The liquid phase leaving this receiver flows into the duct 212 where it is expanded to 20 bars et is fed to the purifying-refrigerating column 101 under the middle packing layer $L_2$.

The vapor phase 213 leaving the receiver 207 is expanded in the turbine expander 214 to 20 bars to reach a temperature of −76° C. It is thereafter injected into the column 101 through the ducts 215 and 217, the said column 101 being reboiled in the cold section of the exchanger 103 (streams 218, 219) from −73° to −60° C.

In column 101, the gas feed contacts the reflux 229 injected into the top 101a, which reflux is constituted by the gaseous distillate issued from the receiver 225 and entirely condensed at −78° C. in the duct 228 passing through the exchanger 103.

The residual gas leaving the column 101 through the duct 230 is heated in the exchanger 103 up to 41.5° C. and is thereafter conveyed through the duct 231 to the compressor 232 coupled with the turbine expander 214. The residual gas which thereafter passes through the duct 234 is compressed in two stages 235 and 236 of the compression section up to a pressure of 66.4 bars, whereas the intermediate exchanger-refrigerating means 241 allows the gas passing through the duct 231 to be cooled from 101° C. to 49° C. The residual gas is cooled in the final exchanger-refrigerating means 238 before being discharged at a pressure of 66 bars.

The condensates at the bottom of the purifying-refrigerating column 101 are discharged by the pump 248 into the duct 249 at a pressure of 22 bars and are thereafter conveyed through the duct 251 to the portion 252 of the exchanger 103 to be heated therein to 13.5° C.

before being fed through 253 to the fractionating column 102 under the upper packing layer $L_{10}$.

The distillate at the top 102a of the column 102 is supplied via the ducts 220, 222 to the exchanger 103 where it is at least partially condensed at 223 to $-23.5°$ C., before being fed through the duct 224 to the receiver 225 to produce a liquid reflux 227, which is injected into the top of the column 102, and a gaseous distillate which is conveyed to the top 101a of the column 101 through the duct 229 after being entirely condensed in the portion 228a of the exchanger 103, as explained earlier.

It should be noted here that it is possible, without departing from the scope of the invention, to integrate the condensation of the column 102 in the top portion of this column, thus of course allowing the receiver 225 and the reflux pump 226 to be done away with. In this case, the negative calories necessary for the condensation will be provided by a cold medium issuing from the plate exchanger 103.

Lastly, the reboiling of the column 102 will be ensured by an external fluid passing through the reboiler 255 (valve V16 open), and the $C_3+$ cut collected in the duct 256 will be at a temperature of 75.6° C. and a pressure of 22 bars.

There will now be described the operation of the apparatus shown in FIG. 2 with a view to obtaining ethane or compounds heavier than ethane ($C_2+$ cut).

In this case, the valves V11, V12, V13, V14 and V15 are opened, whereas the valves V16, V17, V18, V19 and V20 are closed.

The gas dried at 201 at a high pressure and at 15° C. separates into two streams 203 and 205. The stream 205 is partially condensed at 205a at $-62°$ C., thus ensuring the reboiling of the fractionating column 102 in the exchanger 206. As for the stream 203, it is also partially condensed et $-62°$ C. in the portion 204 of the exchanger 103. The streams 205a and 204a are mixed together at 208 before entering the separating receiver 207.

The liquid phase 210 leaving this separator is subcooled at 211 to $-107°$ C. in the plate exchanger 103, and thereafter expanded to 13.8 bars.

The vapor phase 213 leaving the separator 207 is expanded in the turbine expander 214 to 13.8 bars and reaches $-107°$ C. to thereafter pass through the duct 215 before being mixed at 216 with the stream 211 to finally be supplied to the purifying column 101 through the duct 217 between the upper and middle packing layers $L_1$, $L_2$, respectively.

In column 101, the gaseous fraction of the stream 217 contacts the stream 246 which is formed by the recirculation at a high pressure (33.8 bars) of a fraction 244 of the residual gas entirely condensed at 245 in the exchanger 103, the said fraction being withdrawn from the intermediate stage of the compression section 235, 236.

The residual gas leaving the column 101 through the duct 230 is heated in the exchanger 103 to a temperature of 15° C. and is conveyed through the duct 231 to the suction side of the compressor 232 so as to be brought to a pressure from 12.6 to 16.2 bars. The discharge 234 from the compressor 232 is thereafter compressed to 67 bars in both compression stages 235 and 236.

The exchanger-refrigerating means 241 allows refrigerating the gas 239 from 116° C. to 49° C. whereas the residual gas recirculated to the top 101a of the column 101 is withdrawn at the outmet of this exchanger.

The residual gas discharged from the second compression stage 236 is cooled to 49° C. in the final exchanger 238 and is available at a pressure of 66.4 bars.

The condensates issuing from the bottom of the purifying-refrigerating column 101 are fed by the pump 248 directly via the ducts 249 and 250 to the top of the fractionating column 102, whereas the distillates from the top of this column are in their turn conveyed directly to the bottom of the purifying column 101 through the ducts 220, 221.

Lastly, the $C_2+$ cut is collected in the duct 256 provided at the bottom of the fractionating column 102.

There is therefore obtained, according to the invention, a cryogenic extraction process and apparatus which allow extracting, in one and the same unit, either the $C_2+$ cut or the $C_3+$ cut with very high efficiencies capable of reaching 99% for the $C_3+$ cut and 95% for the $C_2+$ cut, it being understood that the switching from one extraction mode to another can be performed very easily and quickly by means of very simple adjustments.

Of course, the invention is not limited to the forms of embodiment described and illustrated which have been given by way of example only.

For instance, it would be perfectly possible, without departing from the scope of the invention, to associate with the turbine expander of the form of embodiment represented in FIG. 2 an additional refrigerating circuit of the type, for example, with several pressure levels.

Otherwise stated, the invention includes all technical means equivalent to the means described as well as their combinations if the latter are carried out according to its gist.

We claim:

1. A process for fractionating a gas feed comprising methane and hydrocarbons heavier than methane in which said heavier hydrocarbons are recovered from said gas feed comprising the steps of:
    (a) Partially condensing said gas feed (106) in a heat-exchange system (103) and feeding said partially condensed feed to the bottom of a contact purifying-refrigerating column (101);
    (b) Withdrawing a residual gas stream (133) from the top of said contact purifying-refrigerating column (101);
    (c) Withdrawing liquid (125) from the bottom of said contact-purifying refrigerating column (101), and feeding said liquid to a fractionation column (102);
    (d) Withdrawing a gaseous distillate (116) from the top of said fractionation column (102), and feeding said distillate to said contact purifying-refrigerating column (101); and
    (e) Withdrawing from the bottom of said fractionation column (102) a stream of hydrocarbons heavier than methane, and selectively producing as said stream of hydrocarbons heavier than methane a stream selected from the group consisting of compounds heavier than methane ($C_2+$ cut) and compounds heavier than ethane ($C_3+$ cut) by, when a $C_3+$ cut is desired:
    (a) Feeding all of said feed gas (106) to said contact purifying-refrigerating column (101);
    (b) Feeding all of the liquid withdrawn from the bottom of said contact purifying-refrigerating column (101) to said fractionation column (102) at a point between its top and bottom; and
    (c) Partially condensing the gaseous distillate withdrawn from the top of said fractionation column (102) in said heat-exchange system (103) and feeding the uncondensed portion of said distillate to the top of said contact purifying-refrigerating column (101); and when a $C_2+$ cut is desired:
(a) Compressing (135) at least part of said residual gas stream (133) and feeding said compressed gas stream (137) to the top of said contact purifying-refrigerating column (101);

when a $C_2+$ cut is desired:
(a) Compressing (135) at least part of said residual gas stream (133) and feeding said compressed gas stream (137) to the top of said contact purifying-refrigerating column (101);
(b) Feeding all of the liquid (125) withdrawn from the bottom of said contact purifying-refrigerating column (101) to the top of said fractionating column (102); and
(c) Feeding all of said gaseous distillate (116) withdrawn from the top of said fractionation column (102), without condensation, to the bottom of said contact purifying-refrigeration column (101).

2. A process according to claim 1, in which, if the cut to be recovered is $C_2+$ cut, the gas feed (106) is at least partially condensed (108) in an exchange system (103), the condensed gas feed is separated (109) into a liquid phase (111) and a gaseous phase (112), said liquid phase (111) is injected into the middle of said fractionating column (102), said gaseous phase (112) is at least partially condensed (113) in said exchange system and then injected (114) into said purifying-refrigerating column (101), and if the cut to be recovered is a $C_3+$ cut, said gas feed (106) is partially condensed (108, 113) in said refrigerating exchange system and then injected (114) directly and without separation into said purifying-refrigerating column (FIG. 1).

3. A process according to claims 1 or 2, wherein cooling in said heat-exchange system (103) is effected by a single refrigerating circuit (105) with several pressure levels and, if the cut to be recovered is a $C_2+$ cut, by a second distinct refrigerating circuit (104) with a single pressure level.

4. A process according to claim 3 wherein the medium in said single refrigerating circuit (105) is a pure hydrocarbon having 3 carbons or a mixture of hydrocarbons having a molecular weight in the range of from 30 to 40.

5. A process according to claim 3 wherein the medium in said second refrigerating circuit (104) is a mixture of light hydrocarbons having a molecular weight ranging from 26 and 36, or is a pure hydrocarbon having 2 carbons.

6. A process according to claim 1 in which, if the cut to be recovered is a $C_2+$ cut, the gas feed (200, 202) is separated into a first portion (205) and a second portion (203), said first portion (205) is used for the purpose of reboiling (206) said fractionating column (102), said second portion (203) is partially condensed (204) in said heat-exchange system (103), said first and second portions are then mixed (208) and the resulting mixture is separated (207) into a liquid phase and a gaseous phase, the liquid phase is subcooled (211) in said exchange system (103), and the gaseous phase (213) is expanded (214) and then mixed (216) with the said subcooled liquid phase (211) to form a combined phase, said combined phase is injected (217) into said purifying-refrigerating column (101), having an upper packing layer ($L_1$), a middle packing layer ($L_2$) and a lower packing layer, at a location below said upper packing layer ($L_1$), and, in which, if the cut to be recovered is a $C_3+$ cut, the entire gas feed (200) is partially condensed (204) in said exchange system (103), and then separated (207) to form a gaseous phase (213) and a liquid phase (210, 212), said gaseous phase (213) is expanded (214) and then injected directly (215, 217) into said column (101) under said upper packing layer, and said liquid phase (210, 212) is injected directly into said purifying-refrigerating column (101) at a location below said middle packing layer ($L_2$) (FIG. 2).

7. A process according to claim 6, wherein additional cooling is provided through a refrigerating circuit having several pressure levels in combination with said expansion (214).

8. A process according to claim 1, wherein said fractionating column (102) operates at a pressure higher than that of said purifying-refrigerating column (101) so as to ensure the injection of the distillate issued from the fractionating column into said purifying-refrigerating column.

9. An apparatus comprising:
(a) a contact purifying-refrigerating column (101);
(b) a fractionating column (102);
(c) a heat-exchange system (103); and
(d) a compressor (135; 232, 235, 236); having
(e) a duct (125, 130, 131, 132; 247, 249, 251, 252 253) communicating between the bottom (101b) of said contact purifying-refrigerating column (101) and said fractionating column (102) and passing through said heat-exchange system (103);
(f) a duct (116, 118, 119, 120; 227, 228, 229) communicating between the top (102a) of said fractionating column (102) and the top (101a) of said contact purifying-refrigerating column (101) and passing through said heat-exchange system (103);
(g) a duct (133, 134; 230, 231) communicating between the top (101a) of said contact purifying-refrigerating column (101) and said compressor (135; 232, 235) and passing through said heat-exchange system (103);
(h) a duct (137, 138, 120; 244, 245, 246) communicating between said compressor (135; 232, 235, 236) and the top (101a) of said contact purifying-refrigerating column (101) and passing through said heat exchange system (103);
(i) a duct (124; 220, 221) communicating between the top (102a) of said fractionating column (102) and the bottom (101b) of said contact refrigerating-purifying column (101) and not passing through said heat-exchange system (103); and
(j) a duct (125, 127, 129; 247, 249, 250) communicating between the bottom (101b) of contact purifying-refrigerating column (101) and the top (102a) of said fractionating column (102) and not passing through said heat-exchange system (103).

10. An apparatus according to claim 9, having a gas feed duct (106, 108) passing through said exchange system (103) and communicating with a separator (109), a duct (111) communicating between the bottom of said separator (109) and the middle of said fractionating column (102), a duct (112, 114) communicating between the top of said separator (109) and said purifying-refrigerating column (101) and which passes through said exchange system (103), and a valve means ($V_1, V_2$) in said gas feed duct (108) to bypass said separator (FIG. 1).

11. An apparatus according to claims 9 and 10, wherein said exchange system (103) includes two closed and independent refrigerating circuits (105, 104) one circuit operating at a single pressure level and the other circuit operating at one or several pressure levels (FIG. 1).

12. An apparatus according to claim 9, having a gas feed duct (202), which is subdivided into first and second gas feed ducts (205 and 203), said first gas feed duct (205) passing through a reboiling system (206) associated with said fractionating column (102), and then joining said second gas feed duct (203, 204) at a junction point (208), a duct (209) communicating between said junction point (208) and a separator (207), a duct (210) connected to the bottom of said separator (207) and communicating with a third and a fourth duct (211, 212), said third duct (211) passes through said exchange system (103) and then communicates with a fifth duct (217) to form a second junction point (216) and said fourth duct (212) communicates directly with said purifying-refrigerating column (101), a duct (213) communicating between the top of said separator (207) and the inlet of a turbine-expander (214), a duct communicating between the outlet of said turbine expander (214) and said second junction point (216), said fifth duct (217) communicating between said second junction point and said purifying-refrigerating column (101) (FIG. 2).

13. An apparatus according to claim 12, having a refrigerating circuit in said heat-exchange system (103) having several pressure levels.

14. An apparatus according to claim 9, wherein said exchange system (103) comprises at least one plate exchanger in which the descending fluids are cooled and the rising fluids are heated.

15. An apparatus according to claim 9, which further comprises a reboiler (159, 160; 219, 219) associated with said purifying-refrigerating column (101) and forming part of said exchange system (103).

16. An apparatus according to claim 9, having means ($V_7$, $V_3$) to selectively direct material removed from the bottom (101b) of said contact purifying-refrigerating column (101) either through said heat-exchange system (103) and to said fractionating column (102), or to the top (102a) of said fractionating column without passing through said heat-exchange system; means ($V_4$, $V_8$) for selectively directing material removed from the top (102b) of said fractionating column (102), either to the top (101a) or to the bottom (101b) of contact purifying-refrigerating column (101); and means ($V_5$) to open or close said duct communicating between said compressor (135) and the top (101a) of said contact purifying-refrigerating column (101).

* * * * *